(12) United States Patent
Keeney et al.

(10) Patent No.: US 10,493,484 B2
(45) Date of Patent: Dec. 3, 2019

(54) APPLICATOR SYRINGE

(71) Applicant: Occam Defense Solutions Inc., Moscow, ID (US)

(72) Inventors: Brian Keeney, Moscow, ID (US); David S. Giessel, Cambridge (CA)

(*) Notice: Subject to any disclaimer, the term of this patent is extended or adjusted under 35 U.S.C. 154(b) by 0 days.

(21) Appl. No.: 16/163,612

(22) Filed: Oct. 18, 2018

(65) Prior Publication Data

US 2019/0118213 A1 Apr. 25, 2019

Related U.S. Application Data (60) Provisional application No. 62/574,287, filed on Oct. 19, 2017.

(51) Int. Cl.
  *B05C 5/02* (2006.01)
  *A61M 5/32* (2006.01)
  *A61M 5/315* (2006.01)

(52) U.S. Cl.
  CPC ........... *B05C 5/02* (2013.01); *A61M 5/31505* (2013.01); *A61M 5/3293* (2013.01)

(58) Field of Classification Search
  CPC .. B05C 5/02; A61M 5/002; F16N 7/00; F41A 29/04
  USPC ........ 222/386, 384, 530, 538; 604/187, 195, 604/192, 193, 110
  See application file for complete search history.

(56) References Cited

U.S. PATENT DOCUMENTS

| | | | | |
|---|---|---|---|---|
| 3,642,000 A | * | 2/1972 | Baker | A61M 31/00 604/218 |
| 4,011,868 A | * | 3/1977 | Friend | A61M 5/31511 604/194 |
| 4,221,218 A | * | 9/1980 | Pfleger | A61M 5/28 604/218 |
| 4,581,023 A | * | 4/1986 | Kuntz | A61M 5/24 604/234 |
| 5,226,894 A | * | 7/1993 | Haber | A61M 5/24 604/198 |
| 5,372,590 A | * | 12/1994 | Haber | A61M 5/002 604/110 |
| 5,769,826 A | * | 6/1998 | Johnson | A61M 5/3232 600/576 |
| 6,352,585 B1 | * | 3/2002 | Diesso | C04B 24/04 106/35 |

(Continued)

*Primary Examiner* — Lien M Ngo
(74) *Attorney, Agent, or Firm* — Asgaard Patent Services, LLC; F. Wayne Thompson, Jr.

(57) ABSTRACT

Implementations of an applicator syringe are provided. In some implementations, the applicator syringe may be configured to dispense a lubricant from a dispensing needle thereof. In some implementations, the applicator syringe may be configured so that the plunger shaft and the dispensing needle are removable when not in use. In some implementations, when the applicator syringe has been disassembled, the dispensing needle may be stored within the barrel of the applicator syringe and the plunger shaft secured about the exterior of the barrel. In some implementations, the applicator syringe may comprise a barrel having a finger flange, a plunger positioned within the interior chamber of the barrel, a plunger shaft configured to urge the plunger forward, a dispensing needle that can be removably secured to the front end of the barrel, a removable cap, and a barrel plug.

11 Claims, 5 Drawing Sheets

(56) References Cited

U.S. PATENT DOCUMENTS

| | | | | |
|---|---|---|---|---|
| RE39,107 E | * | 5/2006 | Shaw | A61B 5/15003 |
| | | | | 600/576 |
| 7,077,826 B1 | * | 7/2006 | Gray | A61M 5/3135 |
| | | | | 604/171 |
| 2006/0229568 A1 | * | 10/2006 | Koopman | A61M 5/31511 |
| | | | | 604/187 |
| 2008/0132851 A1 | * | 6/2008 | Shaw | A61M 5/347 |
| | | | | 604/199 |
| 2016/0296962 A1 | * | 10/2016 | Maxa | B05C 17/00513 |

* cited by examiner

FIG. 7
SECTION B-B
SCALE 1.5 : 1

APPLICATOR SYRINGE

CROSS REFERENCE TO RELATED APPLICATION

This application claims the benefit of U.S. Provisional Application Ser. No. 62/574,287, which was filed on Oct. 19, 2017, and is incorporated herein by reference in its entirety.

TECHNICAL FIELD

This disclosure relates to implementations of an applicator syringe.

BACKGROUND

A syringe is a simple reciprocating pump that includes a plunger and a barrel. The plunger is typically configured to be linearly pulled and pushed within the interior of the barrel, allowing the syringe to take in and expel liquid through a discharge orifice at the front end of the barrel. Often, a dispensing needle, configured to direct the flow into and out of the barrel, is secured to the front end of the barrel.

A lubricant is a substance that is introduced to reduce friction between surfaces in mutual contact, though it may be used for other purposes. Mechanical devices such as firearms rely on appropriately applied lubrication to ensure reliable operation. As such, shooters find it desirable to keep lubrication readily available. However, prior art lubrication dispensers are often too large to conveniently carry, prone to leaking, are not well suited for dispensing a lubricant within the interior of an assembled firearm, or a combination thereof.

Accordingly, it can be seen that needs exist for the applicator syringe disclosed herein. It is to the provision of an applicator syringe that is configured to address these needs, and others, that the present invention in primarily directed.

SUMMARY OF THE INVENTION

Implementations of an applicator syringe are provided. In some implementations, the applicator syringe may be configured to dispense a lubricant from a dispensing needle thereof. In this way, as a non-limiting example, the lubricant may be applied onto the sliding and/or reciprocating parts of a firearm. In some implementations, the applicator syringe may be configured so that the plunger shaft and the dispensing needle are removable when not in use. In some implementations, when the applicator syringe has been disassembled, the dispensing needle may be stored within the barrel of the applicator syringe and the plunger shaft secured about the exterior of the barrel.

In some implementations, the applicator syringe may comprise a barrel, a plunger, a plunger shaft, a dispensing needle, a cap, and a barrel plug. In some implementations, a lubricant (e.g., oil and/or grease) may be stored within the barrel of the applicator syringe.

In some implementations, the front end of the barrel may include a neck portion having a fluid channel therethrough. In some implementations, the neck portion may be configured so the dispensing needle and the cap can be removably secured thereto. In some implementations, the barrel of the applicator syringe may include a finger flange that is located adjacent the back end thereof.

In some implementations, the plunger may be received within the interior chamber of the barrel in a sliding fluid-tight engagement with the cylindrical sidewall thereof. In some implementations, a lubricant may be positioned between the front side of the plunger and the distal end of the fluid channel extending through the neck portion of the barrel.

In some implementations, the plunger shaft may be an elongated hollow cylindrical tube with a longitudinal slit that is made of a resilient material (e.g., a synthetic thermoplastic polymer such as nylon). In some implementations, the two edges of the longitudinal slit may be spread apart, thereby opening the plunger shaft so that it can be secured about the exterior of the barrel. The resilient material of the plunger shaft causes it to hug the exterior of the barrel. In some implementations, the two edges of the longitudinal slit may spring back towards each other when the plunger shaft is removed from the barrel of the applicator syringe. In this way, the plunger shaft may be inserted through an opening in the back end of the barrel and placed into operational contact with the back side of the plunger.

In some implementations, the dispensing needle may comprise a hub and a needle having a lumen therethrough. In some implementations, when the dispensing needle is secured to the neck portion of the barrel, the lumen of the needle is placed into fluid communication with the interior chamber of the barrel via the fluid channel extending through the neck portion. In some implementations, the hub may be configured to removably secure the dispensing needle to the neck portion of the barrel.

In some implementations, the plunger shaft can be used to move the plunger towards the first end of the barrel and thereby expel a portion of the lubricant from the interior chamber, through the fluid channel, and out of the lumen of the dispensing needle.

In some implementations, the cap may be configured to close the opening in the distal end of the fluid channel extending through the neck portion of the barrel. In this way, the lubricant stored within the barrel of the applicator syringe may be prevented from inadvertently leaking out during transportation and/or storage. In some implementations, the cap may be configured so that it can be removably secured to the neck portion of the barrel.

In some implementations, the barrel plug may be inserted into the second end of the barrel and used to block the opening into the interior chamber thereof. In some implementations, the barrel plug may be received within the interior chamber of the barrel in a sliding fluid-tight engagement with the cylindrical sidewall thereof. In some implementations, when the applicator syringe has been disassembled for storage and/or transportation, the dispensing needle may be positioned for storage between the front end of the barrel plug and the back side of the plunger.

In some implementations, the barrel plug may be configured to retain the cap when the cap is not secured to the neck portion of the barrel. In this way, the cap is not easily lost while the applicator syringe is being used to dispense a lubricant contained therein. In some implementations, the front end of the barrel plug may include an opening that is configured to receive and removably retain the front end of the cap therein.

In some implementations, the barrel plug may include a lanyard, the lanyard is configured to secure the barrel plug to the barrel of an applicator syringe. In some implementations, one end of the lanyard may be configured to encircle a portion of the barrel adjacent the flange (or back end) of the applicator syringe. In this way, the barrel plug can be secured to the barrel of the applicator syringe and not easily lost while the applicator syringe is being used to dispense a lubricant contained therein.

BRIEF DESCRIPTION OF THE DRAWINGS

Like reference numerals refer to corresponding parts throughout the several views of the drawings.

DETAILED DESCRIPTION

FIGS. 1-7 illustrate an example applicator syringe 100 according to the principles of the present disclosure. In some implementations, the applicator syringe 100 may be configured to dispense a lubricant 102 from a dispensing needle 140 thereof (see, e.g., FIG. 5). In this way, as a non-limiting example, the lubricant 102 may be applied onto the sliding and/or reciprocating parts of a firearm (e.g., a rifle and/or a handgun). In some implementations, the applicator syringe 100 may be configured so that the plunger shaft 130 and the dispensing needle 140 are removable when not in use (see, e.g. FIG. 1). In some implementations, when the applicator syringe 100 has been disassembled, the dispensing needle 140 may be stored within the barrel 110 of the applicator syringe 100 and the plunger shaft 130 secured about the exterior of the barrel 110 (see, e.g., FIG. 4).

Figure 1:
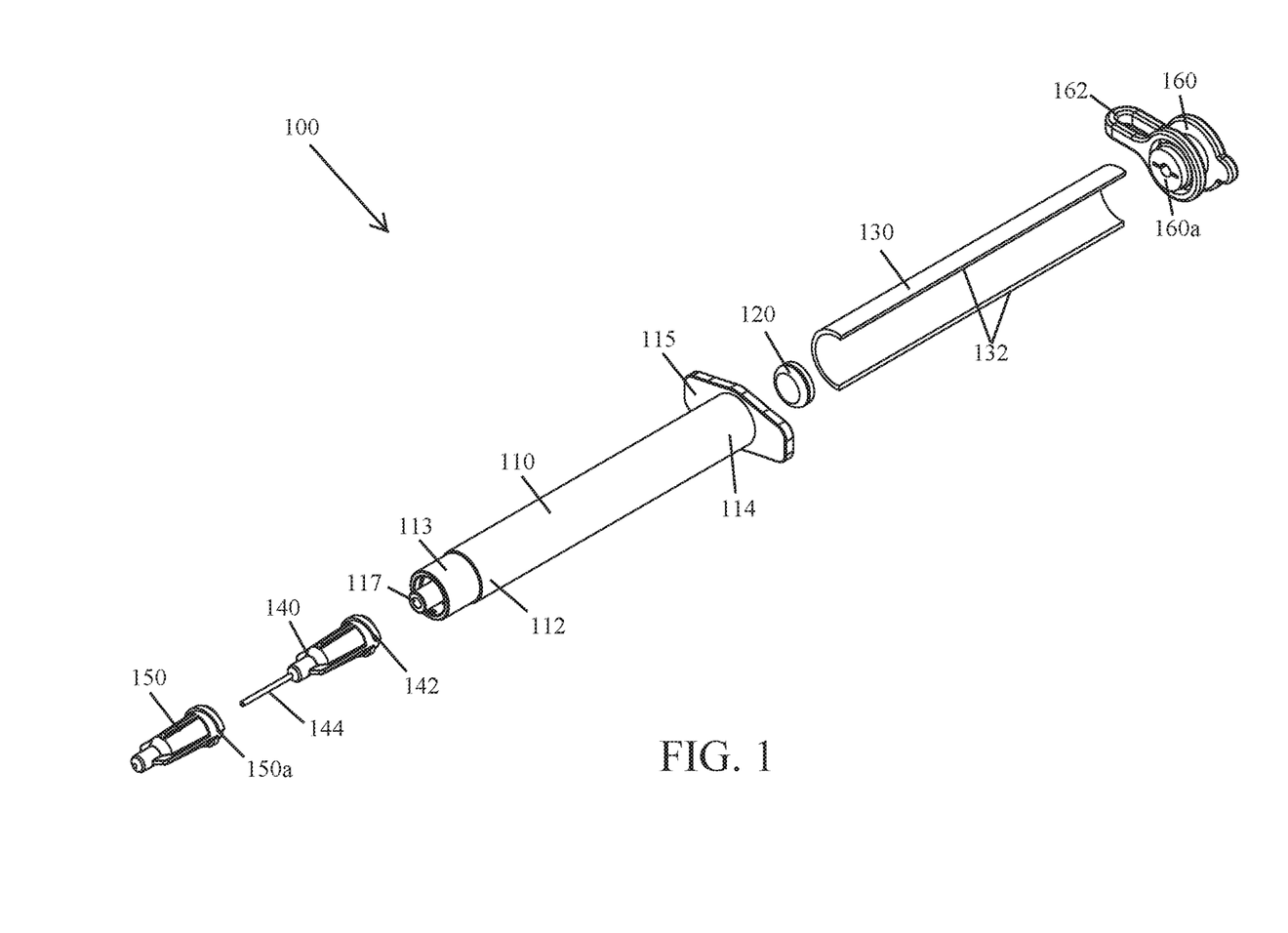
FIG. 1 illustrates an exploded view of an application syringe according to the principles of the present disclosure.

As shown in FIG. 1, in some implementations, the applicator syringe 100 may comprise a barrel 110, a plunger 120, a plunger shaft 130, a dispensing needle 140, a cap 150, and a barrel plug 160. In some implementations, a lubricant 102 (e.g., oil and/or grease) may be stored within the barrel 110 of the applicator syringe 100.

As shown in FIGS. 1-7, in some implementations, the cylindrical barrel 110 of the applicator syringe 100 may comprise a first end 112 (or front end), a second end 114 (or back end), and a cylindrical interior chamber 116.

Figure 4:
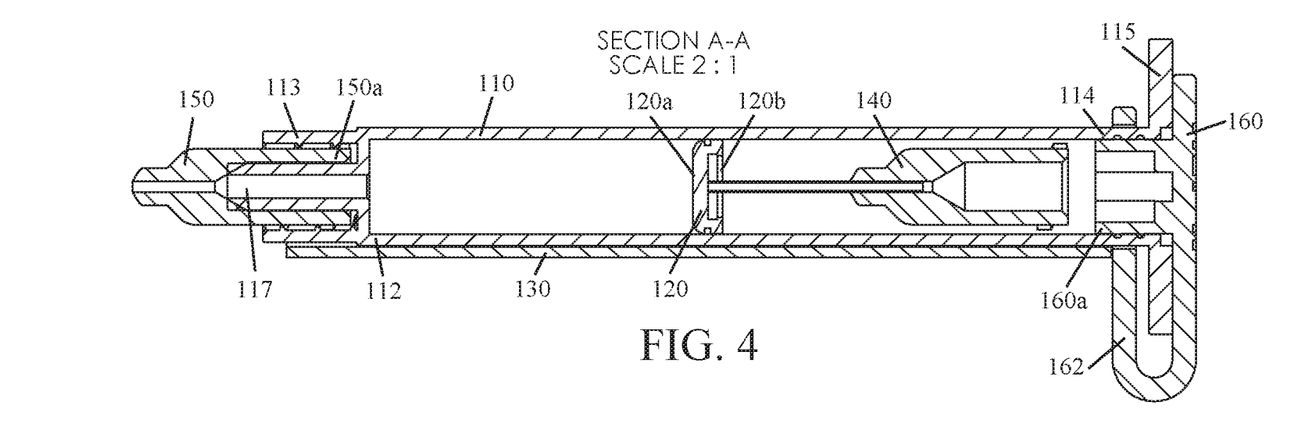
FIG. 4 illustrates a cross-sectional view of the applicator syringe taken along line A-A of FIG. 3.

In some implementations, the first end of the barrel 110 may include a neck portion 113 having a fluid channel 117 therethrough (see, e.g., FIGS. 1 and 4). In some implementations, the neck portion 113 may be configured so the dispensing needle 140 and/or the cap 150 can be removably secured thereto (see, e.g., FIGS. 2 and 5). In some implementations, the neck portion 113 of the barrel 110 may be configured to serve as the male portion of a Luer-lock fitting.

In some implementations, cylindrical barrel 110 may include a finger flange 115 that is located adjacent the second end 114 thereof (see, e.g., FIG. 1). The use of a syringe having a finger flange is well known to those of ordinary skill in the art.

Figure 7:
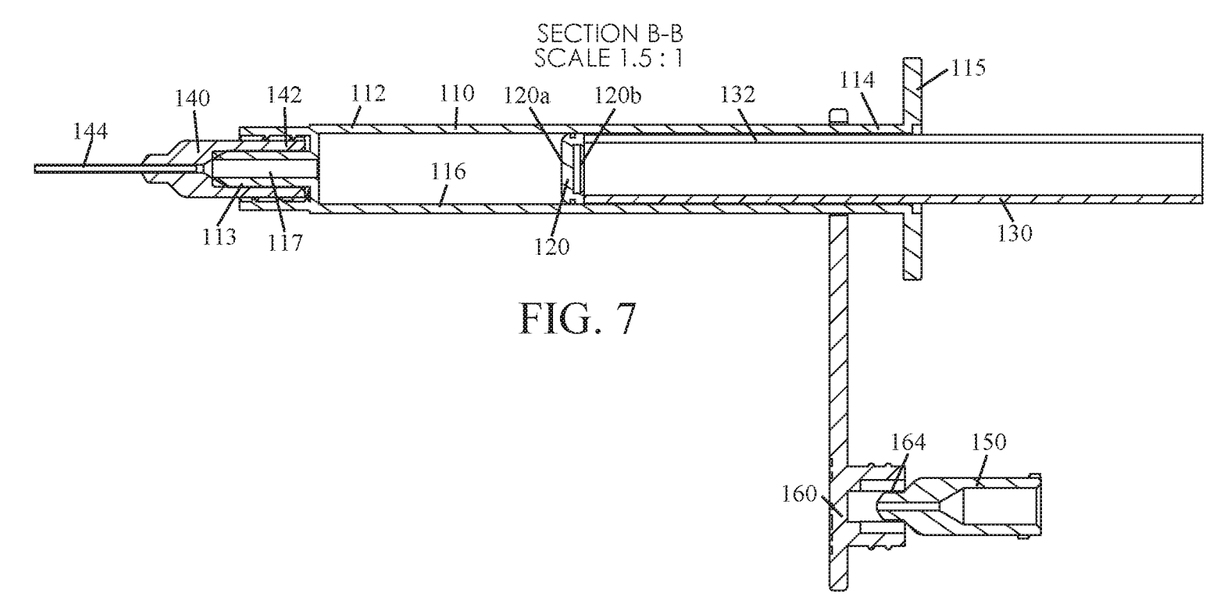
FIG. 7 illustrates a cross-sectional view of the applicator syringe taken along line B-B of FIG. 6.

As shown in FIGS. 4 and 7, in some implementations, the plunger 120 may be received within the interior chamber 116 of the barrel 110 in a sliding fluid-tight engagement with the cylindrical sidewall thereof. In some implementations, the plunger 120 may comprise a first side 120a (or front side) and a second side 120b (or back side). In some implementations, the lubricant 102 may be positioned between the first side 120a of the plunger 120 and the distal end of the fluid channel 117 extending through the neck portion 113 of the barrel 110.

Figure 2:
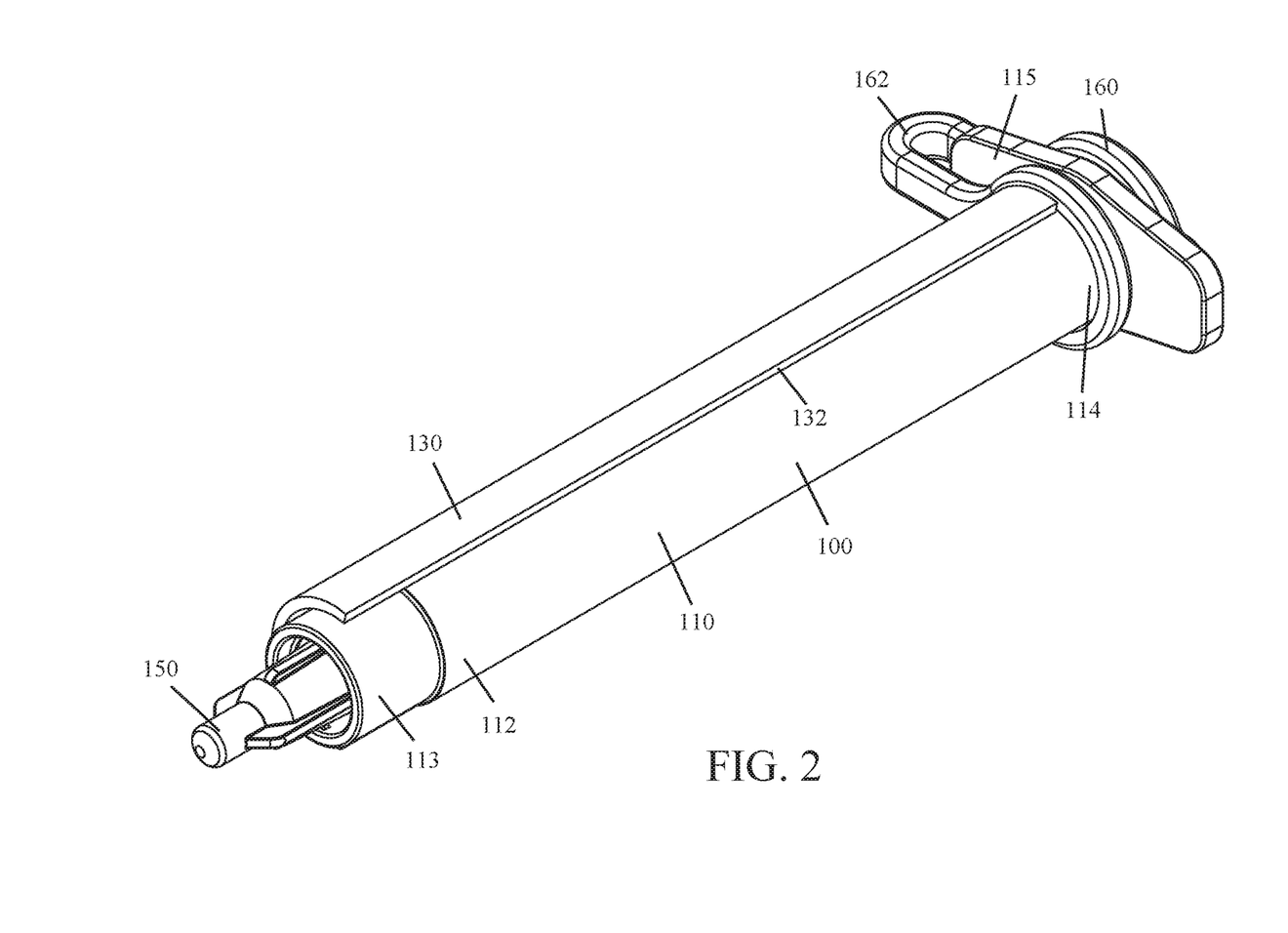
FIG. 2 illustrates a side perspective view of the applicator syringe shown in FIG. 1, wherein the applicator syringe is shown disassembled for storage and/or transportation.

As shown in FIGS. 1 and 2, in some implementations, the plunger shaft 130 may be an elongated hollow cylindrical tube with a longitudinal slit 132. In some implementations, the plunger shaft 130 may be made of a resilient material (e.g., a synthetic thermoplastic polymer such as nylon). In some implementations, the two edges of the longitudinal slit 132 may be spread apart, thereby opening the plunger shaft 130 so that it can be secured about the exterior of the barrel 110 (see, e.g., FIG. 2). The resilient material of the plunger shaft 130 causes it to hug the exterior of the barrel 110. In some implementations, the two edges of the longitudinal slit 132 may spring back towards each other when the plunger shaft 130 is removed from the barrel 110 of the applicator syringe 100. In this way, the plunger shaft 130 can be inserted through an opening in the second end 114 of the barrel 110 and placed into operational contact with the second side 120b of the plunger 120 (see, e.g., FIG. 7).

As shown in FIG. 2, in some implementations, when the plunger shaft 130 is secured about the exterior of an applicator syringe 100, the plunger shaft 130 may extend between the first end 112 and the second end 114 of the barrel 110. In some implementations, when the plunger shaft 130 is secured about the exterior of an applicator syringe 100, the plunger shaft 130 may be long enough to envelope and protect a dispensing needle 140 secured to the neck portion 113 of the barrel 110 (not shown).

As shown in FIGS. 1 and 7, in some implementations, the dispensing needle 140 may comprise a hub 142 and a blunt needle 144 having a lumen therethrough. In some implementations, the dispending needle 140 may be removably secured to the neck portion 113 of the barrel 110. In this way, the lumen of the needle 144 can be placed into fluid communication with the interior chamber 116 of the barrel 110 via the fluid channel 117 extending through the neck portion 113. In some implementations, the hub 142 may be configured to removably secure the dispensing needle 140 to the neck portion 113 of the barrel 110. In some implementations, the hub 142 of the dispensing needle 140 may be configured to serve as the female portion of a Luer-lock fitting. In this way, a leak-free connection between the hub 142 of the dispending needle 140 and the neck portion 113 of the barrel 110 can be established.

In some implementations, the hub 142 of the dispensing needle 140 may be secured to the neck portion 113 of the barrel 110 by a friction fit between the parts (not shown). In some implementations, the hub 142 of the dispensing needle 140 and the neck portion 113 of the barrel 110 may be compatible Luer-slip fittings configured to be pressed together and held by friction. In this way, a leak-free connection between the hub 142 of the dispending needle 140 and the neck portion 113 of the barrel 110 can be established. In some implementations, when the dispensing needle 110 is held in position by a friction fit, the applicator syringe 100 may not include a barrel plug 160.

Figure 5:
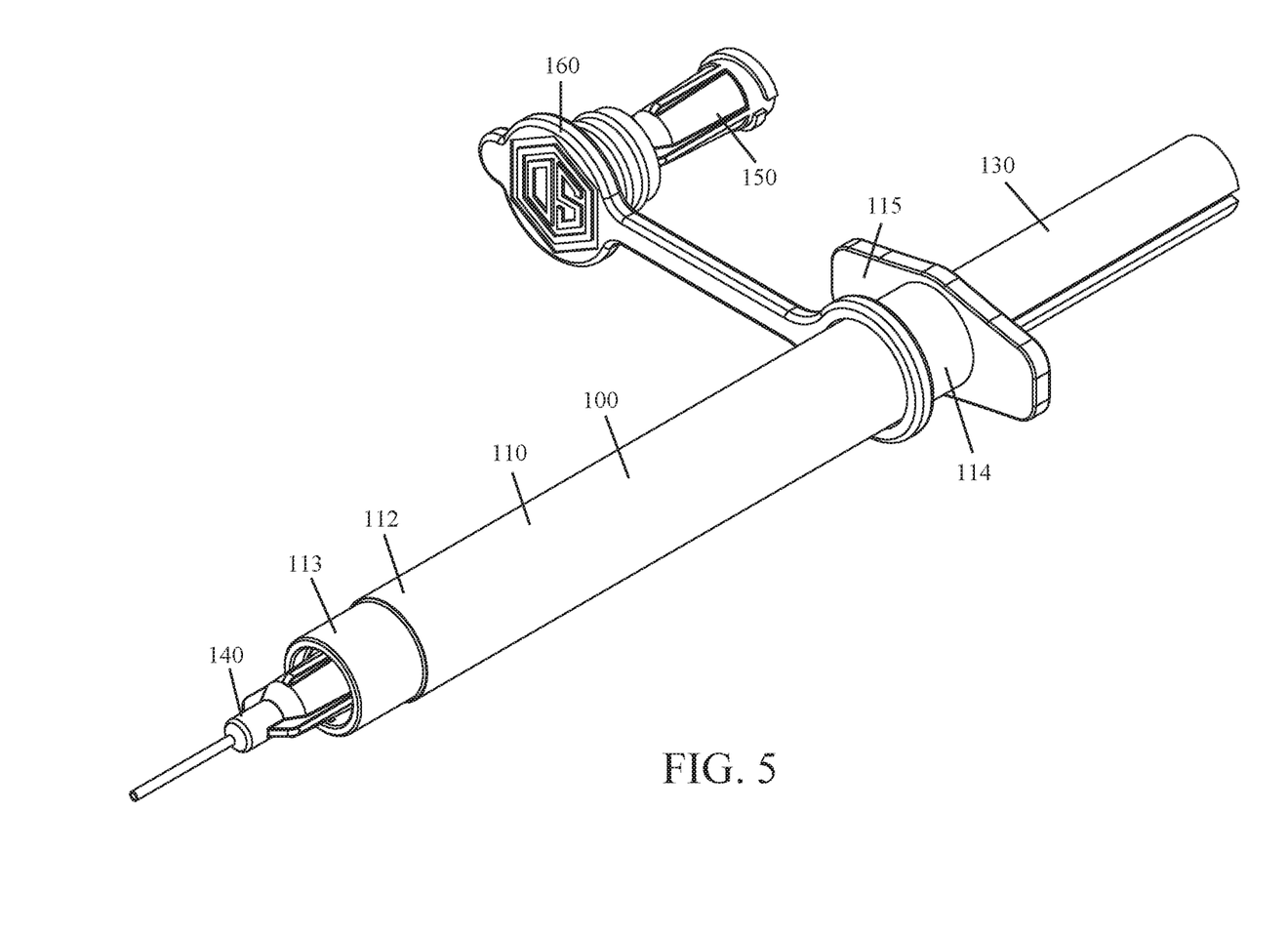
FIG. 5 illustrates a side perspective view of the applicator syringe shown in FIG. 1, wherein the applicator syringe is shown assembled for use.
Figure 6:
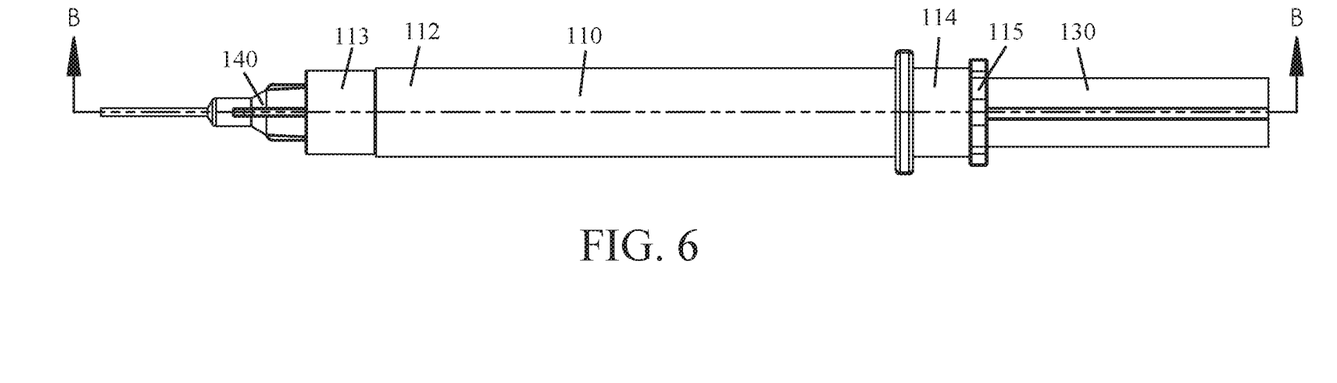
FIG. 6 illustrates a side view of the applicator syringe shown in FIG. 5.

As shown in FIGS. 5-7, in some implementations, the plunger shaft 130 can be used to move the plunger 120 towards the first end 112 of the barrel 110 and thereby expel a portion of the lubricant 102 from the interior chamber 116, through the fluid channel 117, and out of the lumen of the dispensing needle 140.

Figure 3:
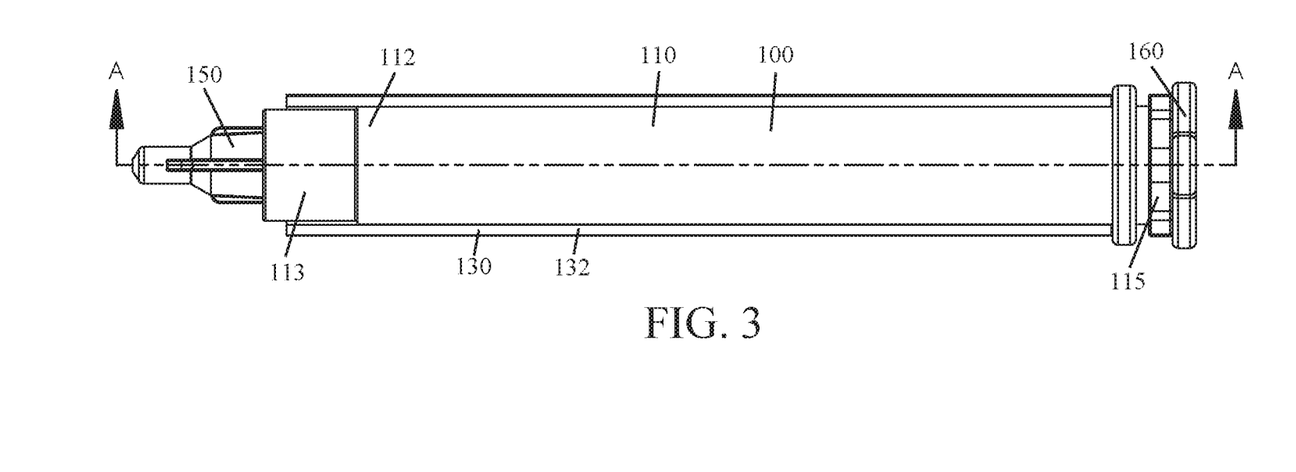
FIG. 3 illustrates a side view of the applicator syringe shown in FIG. 2.

As shown in FIGS. 2-4, in some implementations, the cap 150 may be used to close the opening in the distal end of the fluid channel 117 extending through the neck portion 113 of the barrel 110. In this way, the lubricant 102 stored within the barrel 110 of the applicator syringe 100 may be prevented from inadvertently leaking out during transportation and/or storage. In some implementations, the cap 150 may be removably secured to the neck portion 113 of the barrel 110. In some implementations, the proximal end 150a of the cap 150 may be configured to removably secure the cap 150 to the neck portion 113 of the barrel 110. In some implementations, the proximal end 150a of the cap 150 may be configured to serve as the female portion of a Luer-lock fitting. In this way, a leak-free connection between the proximal end 150a of the cap 150 and the neck portion 113 of the barrel 110 can be established.

As shown in FIGS. 2-4, in some implementations, the barrel plug 160 may be inserted into the second end 114 of the barrel 110 and used to block the opening into the interior chamber 116 thereof. In some implementations, the barrel plug 160 may be received within the interior chamber 116 of the barrel 110 in a sliding fluid-tight engagement with the cylindrical sidewall thereof. In some implementations, when the applicator syringe 100 has been disassembled for storage and/or transportation, the dispensing needle 140 may be positioned for storage between the front end 160a of the barrel plug 160 and the back side 120b of the plunger 120 (see, e.g., FIG. 4).

As shown in FIGS. 5 and 7, in some implementations, barrel plug 160 may be configured to retain the cap 150 when it is not secured to the neck portion 113 of the barrel 110. In this way, the cap 150 is not easily lost while the applicator syringe 100 is being used to dispense a lubricant contained therein. In some implementations, the front end 160a of the barrel plug 160 may include an opening 164 that is configured to receive and removably retain a distil end (or front end) of the cap 150 therein (see, e.g., FIG. 7). In some implementations, the barrel plug 160 may not be configured to retain the cap 150 of an applicator syringe 100 (not shown).

As shown in FIGS. 2 and 5, in some implementations, the barrel plug 160 may include a lanyard 162, the lanyard 162 is configured to secure the barrel plug 160 to the barrel 110 of an applicator syringe 100. In some implementations, one end of the lanyard 162 may be configured to encircle a portion of the barrel 110 adjacent the flange 115 (or back end) of the applicator syringe 100. In this way, the barrel plug 160 can be secured to the barrel 110 of the applicator syringe 100 and not easily lost while the applicator syringe 100 is being used to dispense the lubricant 102 contained therein. In some implementations, the barrel plug 160 may not include a lanyard (not shown).

In some implementations, the needle 144 may have a point profile other than blunt. In some implementations, the needle 144 may have any point profile suitable for dispensing a lubricant.

In some implementations, an applicator syringe 100 may be used to contain and/or dispense an abrasive compound, medications, other single-phase fluids (gas or liquid), and/or multi-phase fluids (e.g., gas, liquid, solid) suitable for being dispensed from a syringe. In some implementations, an applicator syringe 100 may be used to dispense the contents thereof for a purpose other than the application of a lubricant onto the sliding and/or reciprocating parts of a firearm.

Reference throughout this specification to "an embodiment" or "implementation" or words of similar import means that a particular described feature, structure, or characteristic is included in at least one embodiment of the present invention. Thus, the phrase "in some implementations" or a phrase of similar import in various places throughout this specification does not necessarily refer to the same embodiment.

Many modifications and other embodiments of the inventions set forth herein will come to mind to one skilled in the art to which these inventions pertain having the benefit of the teachings presented in the foregoing descriptions and the associated drawings.

The described features, structures, or characteristics may be combined in any suitable manner in one or more embodiments. In the above description, numerous specific details are provided for a thorough understanding of embodiments of the invention. One skilled in the relevant art will recognize, however, that embodiments of the invention can be practiced without one or more of the specific details, or with other methods, components, materials, etc. In other instances, well-known structures, materials, or operations may not be shown or described in detail.

While operations are depicted in the drawings in a particular order, this should not be understood as requiring that such operations be performed in the particular order shown or in sequential order, or that all illustrated operations be performed, to achieve desirable results.

The invention claimed is:

1. An applicator syringe configured to dispense a lubricant, the applicator syringe comprising:
   a barrel, the barrel comprises an interior chamber and a neck portion having a fluid channel therethrough;
   a plunger having a front side and a back side, the plunger is configured to be received within the interior chamber of the barrel in a sliding fluid-tight engagement with a cylindrical sidewall thereof;
   a plunger shaft configured to be removably secured about the exterior of the barrel, the plunger shaft is an elongated hollow cylindrical tube with a longitudinal slit that is made of a resilient material;
   a dispensing needle removably secured to the neck portion of the barrel, the dispensing needle comprises a needle having a lumen that extends therethrough;
   a cap, the cap is configured to be removably secured to the neck portion of the barrel and thereby block the opening in a distal end of the fluid channel;
   a removable barrel plug, the barrel plug is configured to block an opening in a back end of the barrel that allows access to the interior chamber thereof, the barrel plug is also configured to retain the cap when the cap is not secured to the neck portion of the barrel;
   wherein the lumen of the dispensing needle is in fluid communication with the interior chamber of the barrel while the dispensing needle is secured to the neck portion thereof; and
   wherein the plunger shaft can be used to move the plunger towards a front end of the barrel and thereby expel a portion of lubricant from within the interior chamber of the barrel.

2. The applicator syringe of claim 1, wherein the dispensing needle is configured to be removably secured to the neck portion of the barrel.

3. The applicator syringe of claim 2, wherein the dispensing needle further comprises a hub, the hub is configured to removably secure the dispensing needle to the neck portion of the barrel.

4. The applicator syringe of claim 1, wherein the barrel further comprises a finger flange.

5. The applicator syringe of claim 1, wherein two edges of the longitudinal slit spring back towards each other when the plunger shaft is removed from the exterior of the barrel, thereby allowing the plunger shaft to be inserted through an opening in a back end of the barrel and placed into operational contact with the back side of the plunger.

6. The applicator syringe of claim 1, further comprising a lubricant, the lubricant is stored within the interior chamber of the barrel, between the front side of the plunger and the distal end of the fluid channel.

7. The applicator syringe of claim 1, wherein a portion of the barrel plug is received within the interior chamber of the barrel in a sliding fluid-tight engagement with the cylindrical sidewall thereof.

8. The applicator syringe of claim 1, wherein the barrel plug includes a lanyard, the lanyard is configured to secure the barrel plug to the barrel of the applicator syringe.

9. The applicator syringe of claim 1, wherein a front end of the barrel plug includes an opening that is configured to receive and removably retain a front end of the cap therein.

10. A method of using an applicator syringe, the method comprising:
providing an applicator syringe comprising: a barrel, the barrel comprises an interior chamber and a neck portion having a fluid channel therethrough; a plunger having a front side and a back side, the plunger is configured to be received within the interior chamber of the barrel in a sliding fluid-tight engagement with a cylindrical sidewall thereof; a plunger shaft, the plunger shaft is configured to be removably secured about the exterior of the barrel, the plunger shaft is also configured to be inserted into the interior chamber of the barrel through an opening in a back end thereof when removed from the exterior of the barrel, the plunger shaft is an elongated hollow cylindrical tube with a longitudinal slit that is made of a resilient material; a dispensing needle configured to be removably secured to the neck portion of the barrel, the dispensing needle comprises a needle having a lumen that extends therethrough; wherein the lumen of the dispensing needle is placed into fluid communication with the interior chamber of the barrel when the dispensing needle is secured to the neck portion of the barrel; a cap, the cap is configured to be removably secured to the neck portion of the barrel and thereby block the opening in a distal end of the fluid channel; and a removable barrel plug, the barrel plug is configured to block the opening in the back end of the barrel that allows access to the interior chamber thereof, the barrel plug is also configured to retain the cap when the cap is not secured to the neck portion of the barrel;

securing the cap to the neck portion of the barrel;

placing the dispensing needle within the interior chamber of the barrel; and inserting the barrel plug into the opening in the back end of the barrel, thereby positioning the dispensing needle between the back side of the plunger and a front end of the barrel plug.

11. The method of claim 10 further comprising, securing the plunger shaft about the exterior of the barrel.

* * * * *